US008785380B2

(12) United States Patent
Madhavamenon et al.

(10) Patent No.: US 8,785,380 B2
(45) Date of Patent: Jul. 22, 2014

(54) FORMULATION CONTAINING CURCUMINOIDS EXHIBITING ENHANCED BIOAVAILABILITY

(75) Inventors: Krishnakumar Illathu Madhavamenon, Kerala (IN); Abhilas Ravi, Kerala (IN); Dinesh Kumar, Kerala (IN); Balu Paulose Maliakel, Kerala (IN)

(73) Assignee: M/S Akay Flavours & Aromatics Pvt Ltd., Cochin, Kerala (IN)

( * ) Notice: Subject to any disclaimer, the term of this patent is extended or adjusted under 35 U.S.C. 154(b) by 0 days.

(21) Appl. No.: 13/360,005

(22) Filed: Jan. 27, 2012

(65) Prior Publication Data

US 2013/0029905 A1  Jan. 31, 2013

(30) Foreign Application Priority Data

Feb. 1, 2011  (IN) .............................. 370/CHE/2010

(51) Int. Cl.
 A61K 38/16 (2006.01)
 A61P 3/02 (2006.01)
 A61K 36/48 (2006.01)
(52) U.S. Cl.
 CPC ............. *A61K 36/48* (2013.01); *A61K 2236/30* (2013.01)
 USPC ....................................................... 514/5.5
(58) Field of Classification Search
 None
 See application file for complete search history.

(56) References Cited

U.S. PATENT DOCUMENTS

| | | | | |
|---|---|---|---|---|
| 5,997,877 | A | * | 12/1999 | Chang ........................... 424/757 |
| 2005/0238738 | A1 | * | 10/2005 | Lee et al. ....................... 424/757 |
| 2007/0148263 | A1 | | 6/2007 | Antony |

FOREIGN PATENT DOCUMENTS

| | | |
|---|---|---|
| WO | WO 2007/101551 | 9/2007 |
| WO | WO 2007/103435 | 9/2007 |
| WO | WO 2010038237 A2 * | 4/2010 |

OTHER PUBLICATIONS

Anand et al. Molecular Pharmaceutics. vol. 4(6);p. 807-818:2007.*
Zheng et al. Langmuir. vol. 26(11);p. 7679-7681:2010.*
Curcumin. Method used to determine purity by Joint Expert Committee on Food Additives (JECFA), 2003.
Anand, Pretha, Kunnumakkara, Ajaikumar B, Newman, Robert A. and Aggarwal, Bharat B. "Bioavailability of Curcumin: Problems and Promises," *Molecular Pharmaceutics*, Nov. 14, 2007. ACS Publications. Downloaded from http://pubs.asc.org on Apr. 2, 2009.
Begum, Aynun N., Jones, Mychica R, Lim, Giselle P., Morihara, Takashi, Kim, Peter, Heath, Dennis D., Rock, Cheryl L., Pruitt, Mila A., Yang, Fusheng, Hudspeth, Beverly, Hu, Shuxin, Faull, Kym F., Teter, Bruce, Cole, Greg M. and Frautschy, Sally A. "Curcumin Structure-Function, Bioavailability, and Efficacy in Models of Neuroinflamation and Alzheimer's Disease." *The Journal of Pharmacology and Experimental Therapeutic*, vol. 326, No. 1, pp. 196-208, 2008.
Chuang, S.E., Kuo, M.L., Hsu, C.H., Chen, C.R., Lin, J.K., Lai, G.M., Hsieh, C.Y. and Cheng, A.L. "Curcumin-containing diet inhibits diethylnitrosamine-induced Murine hepatocarcinogenesis." *Carcinogenesis* (2000) 21 (2): 331-335. doi: 10.1093/carcin/21.2.331.
Garcea, G., Jones, D.J.L., Singh, R., Dennison, A.R., Farmer, P.B., Sharma, R.A. , Steward, W.P., Gescher, A.J. and Berry, D.P. "Detection of curcumin and its metabolites in hepatic tissue and portal blood of patients following oral administration." *British Journal of Cancer*, 2004, vol. 90, pp. 1011-1015.
Garcea, Giuseppe, Berry, David P., Jones, Donald J.L., Singh, Raj, Dennison, Ashley R., Farmer, Peter B., Sharma, Ricky a., Steward, William P. and Gescher, Andreas J. "Consumption of the Putative Chemopreventive Agent Curcumin by Cancer Patients: Assessment of Curcumin Levels in the Colorectum and their Pharmacodynamic Consequences." *Cancer Epidemiology, Biomarkers & Prevention*, 2005, vol. 14, pp. 120-125. Published online Jan. 24, 2005. Downloaded from cebp.aacrjournals.org on Jan. 11, 2012.
Inano, Hiroshi, Onoda, Makoto, Inafuku, Naoshi, Kubota, Megumi, Kamada, Yasuhiro, Osawa, Toshihiko, Kobayashi, Hisae and Wakabayashi, Katsumi. "Potent preventative action of curcumin on radiation-induced initiation of mammary tumorigenesis in rats." *Carcinogenesis*, 2000, vol. 21, No. 10, pp. 1835-1841.
Ireson, Christopher R., Jones, Donald J.L., Orr, Samantha, Coughtrie, Michael W.H., Boocock, David J., Williams, Marion L., Farmer, Peter B., Steward, William P. and Gescher, Andreas J. "Metabolism of the Cancer Chemopreventive Agent Curcumin in Human and Rat Intestine." *Cancer Epidemiology, Biomarkers & Prevention*, Jan. 2002, vol. 11, pp. 106-111.
Jurenka, Julie S. "Anti-inflammatory Properties of Curcumin, a Major Constituent of *Curcuma longa*: A Review of Preclinical and Clinical Research." *Alternative Medicine Review*, vol. 14, No. 2, 2009.
Kocisko, David A., Baron, Gerald S., Rubenstein, Richard, Chen, Jiancao, Kuizon, Salomon and Caughey, Byron. "New Inhibitors of Scrapie-Associated Prion Protein Formation in a Library of 2,000 Drugs and Natural Products." *Journal of Virology*, Oct. 2003, pp. 10288-10294.

(Continued)

*Primary Examiner* — Karlheinz R Skowronek
*Assistant Examiner* — Schuyler Milton
(74) *Attorney, Agent, or Firm* — D. Peter Hochberg; Sean F. Mellino; Richard A. Wolf (57) ABSTRACT

The present invention relates to a formulation containing curcuminoids exhibiting enhanced in vivo bioavailability and resultant improved efficacy, said formulation comprising curcuminoids and a gel forming, non digestive and soluble dietary polysaccharide fiber galactomannan matrix and proteins derived from fenugreek [*Trigonella Foenum graecum*]. The invention also relates to a process for producing the formulation and extracting non-digestible soluble dietary polysaccharide fiber galactomannans containing proteins from fenugreek seeds.

12 Claims, 8 Drawing Sheets

(56) References Cited

OTHER PUBLICATIONS

Li, Mao, Zhang, Zhuo, Hill, Donald L., Wang, Hui and Zhang, Ruiwen. "Curcumin, a Dietary Component, Has Anticancer, Chemosensitization, and Radiosensitization Effects by Down-regulating the MDM2 Oncogene through the P13K/mTOR/ETS2 Pathway." *Cancer Research*, 2007; 67: (5). Mar. 1, 2007, pp. 1988-1996.

Marczylo, Timothy H., Verschoyle, Richard D., Cooke, Darren N., Morazzoni, Paolo, Steward, William P. and Gescher, Andreas J. Comparison of systemic availability of Curcumin with that of curcumin formulated with phosphatidylcholine. *Cancer Chemother Pharmacol* (2007) 60:171-177.

Pan, Min-Hsiung, Huang, Tsang-Miao and Lin, Jen-Kun. "Biotransformation of Curcumin Through Reduction and Glucuronidation in Mice." *Drug Metabolism and Disposition*, 1999, vol. 27, No. 1, pp. 486-494.

Patel, Mayur M., Patel, Santnu L., Bhadani, Manish N., Shah, Tejal and Amin, Avani F. "A synchronous colon-specific drug delivery system for orally Administered mesalamine." *Acta Pharmaceutica Sciencia*, (2009) 51: 251-260.

Perkins, Sarah, Verschoyle, Richard D., Hill, Kirsti, Parveen, Ifat, Threadgill, Michael D., Sharma, Ricky A., Williams, Marion L., Steward, William P. and Gerscher, Andreas J. "Chemopreventive Efficacy and Pharmacokinetics of Curcumin in the Min/+ Mouse, a Model of Familial Adenomatous Polyposis." *Cancer Epidemiology, Biomarkers & Prevention*, 2002, vol. 11, pp. 535-540. Downloaded from cebp.aacrjournals.org on Jan. 11, 2012.

Sharma, Ricky A., McLelland, Heather R., Hill, Kirsti A., Ireson, Christopher R., Euden, Stephanie A., Manson, Margaret M., Pirmohamed, Munir, Marnett, Lawrence J., Gescher, Andreas J. and Steward, William P. "Pharmacodynamic and Pharmacokinetic Study of Oral *Curcuma* Extract in Patients with Colorectal Cancer." *Clinical Cancer Research*, Jul. 2001, vol. 7, pp. 1894-1900. Downloaded from clincancerres.aacrjournals.org on Jan. 11, 2012.

Sharma, Ricky A., Euden, Stephanie A., Platton, Sharon L., Cooke, Darren N., Shafayat, Aisha, Hewitt, Heather R., Marczylo, Timothy H., Morgan, Bruno, Hemmingway, David, Plummer, Simon M., Pirmohamed, Munir, Gescher, Andreas J. and Steward, William P. "Phase I Clinical Trial of Oral Curcumin: Biomarkers of Systemic Activity and Compliance." *Clinical Cancer Research*, Oct. 15, 2004, vol. 10, pp. 6847-6854. Downloaded from clincancerres.aacrjournals.org on Jan. 11, 2012.

Yang, Fusheng, Lim, Giselle P., Begum, Aynun N., Ubeda, Oliver J., Simmons, Mychica R., Ambegaokar, Surendra S., Chen, Pingping, Kayed, Rakez, Glabe, Charles G., Frautschy, Salley A. and Cole, Gregory M. "Curcumin Inhibits Formation of Amyloid β Oligomers and Fibrils, Binds Plaques, and Reduces Amyloid in Vivo." *The Journal of Biological Chemistry*, vol. 280, No. 7, Feb. 18, 2004, pp. 5892-2005. Published, JBC Papers in Press, Dec. 7, 2004.

\* cited by examiner

|  | Sample administered | Subjects (n) | Dose (mg) | $C_{max}$ (µg/g) | $T_{max}$ (h)[d] | $C24_{max}$ (µg/g) | AUC (µg/g.h) |
|---|---|---|---|---|---|---|---|
| Animals | Unformulated curcumin | 16 | 250 mg/kg | 0.02±0.006 | 3.0 | 0.008±0.006 | 1039±118 |
|  | Formulated curcumin[a] | 16 | 250 mg/kg | 0.70±0.13 | 5.0 | 0.21±0.07 | 20777±867 |
| Humans | Unformulated curcumin | 8 | 1000 mg | 0.022±0.01 | 0.5 | 0.004±0.002 | 510±123 |
|  | Formulated curcumin[b] | 8 | 250 mg | 0.29±0.11 | 1.0 | 0.042±0.008 | 6587±234 |
|  | Formulated curcumin[c] | 8 | 1500 mg | 0.37±0.18 | 1.0 | 0.048±0.004 | 8100±287 |

[a]250 mg/kg formulated curcumin is equivalent to only 100 mg/kg unformulated curcumin, [b]250 mg formulated curcumin contains 100 mg unformulated curcumin and [c]1500 mg formulated curcumin was equivalent to 600 mg unformulated curcumin. [d]$T_{max}$ was deduced from the plasma concentration-time plots.

FORMULATION CONTAINING CURCUMINOIDS EXHIBITING ENHANCED BIOAVAILABILITY

CROSS-REFERENCE TO RELATED APPLICATION

This application claims foreign priority based on Indian Application Serial No. 370/CHE/2010, filed on Feb. 1, 2011, the content of which is incorporated herein by reference in its entirety.

BACKGROUND OF THE INVENTION

1. Field of the Invention

The present invention relates to a novel formulation for enhancing the bioavailability of curcuminoids comprising an extensive gel forming non digestible but fermentable soluble dietary polysaccharide fiber galactomannan containing proteins purified from the well known spice, fenugreek. The invention also relates to a method of making a formulation of curcuminoids. The method involves impregnation of curcuminoids in a soluble fiber matrix to produce microencapsulates which possess a unique binding and enhanced solubility and compatibility under gastrointestinal conditions to protect the curcuminoids in the upper gastrointestinal tract and facilitate its slow release in the colon for better absorption. The invention helps in overcoming the poor systematic bioavailability upon oral administration which differ significantly in its properties with regard to efficacy was demonstrated in animals and human volunteers.

2. Description of the Prior Art

Curcuminoids, (a mixture of polyphenolic phytochemicals viz., curcumin, demethoxycurcumin and bisdemethoxycurcumin, hereinafter referred to as curcumin) is obtained from the common curry spice, turmeric (*Curcuma longa* L). It has been scientifically researched that curcumin has effective therapeutic properties. It acts as an antioxidant, anti-inflammatory, antispasmodic, anticoagulant, anticarcinogenic, and is involved in immunomodulatory activities and heals wounds. It is hepato- and nephro protector with strong capacity to reduce proliferation of a variety of malignant and normal cells, to induce apoptosis and to suppress tumour initiation, promotion and metastasis. In Caughey et. al., (J Virol. 2003, 77(19): 10288-94) it is stated that curcumin is one of the most effective natural molecule for many dreadful ailments and age related diseases ever tested in vitro, although it did not work in vivo with oral dosing of unstated formulation.

Curcumin has shown to act mainly by down regulating the transcription factors like NF-kB which leads to decreased gene expression of cytokines (TNF-α, IL-1β, iNOS), chemokines (MCP-1), and other inflammatory proteins (COX-2) that are critical mediators in inflammatory diseases (Jurenka J S et al 2009). Curcumin's activity as anticancer, chemosensitization, and radiosensitization agent has been shown to be by down-regulating the MDM2 oncogene through the PI3K/mTOR/ETS2 Pathway (Li et al., 2007). In the case of Alzheimer's disease curcumin offers its benefit by effectively chelating with amyloid plaques forming peptides, chelating metal ions that cause lipid, protein and DNA oxidative damage and inhibiting NF-kB transcription and the production of TNF-α, under conditions of oxidative damage and inflammation (Yang et al, 2005).

The limiting factor of curcumin despite its immense therapeutic effectiveness is due to its poor absorption in the Gastrointestinal tract, which reduces its bioavailability. When taken orally, only traces of curcumin appear in the blood, whereas most of the dose is excreted through the feces. Sharma et. al. (*Clin Cancer Res* 2004, 10(20), 6847-54) states that most curcumin activities require 0.1-2 micromolar levels in vitro, but current supplements result only in negligible, low nanomolar blood levels. It is also stated in Garcea G et. al, (*Br J Cancer*, 2004, 90(5): 1011-15) that Sharma's group at Leicester has tried repeatedly and has been unable to achieve significant blood levels beyond the low nanomolar range. They also conclude that delivery of effective concentrations of oral curcumin to systematic tissues (outside the GI tract) is "probably not feasible".

In Sharma R. A et. al., (*Clin. Cancer res.*, 2001, 7:1834-1900) it is shown that curcumin bioavailability in humans is poor, as seen from the results of a pilot study of standardized turmeric extract in colorectal cancer patients. In Pan, M. H et. al, (*Drug Metabol. Dispos.*, 1999, 27: 486-94) it is stated that curcumin undergoes rapid metabolic O-conjugation to curcumin glucronide and curcumin sulfate and bioreduction to tetrahydrocurcumin, hexahydrocurcumin and hexahydrocurcuminol in rats and mice in vivo. Metabolic conjugation and reduction of curcumin was more in human than in rat intestinal tissue (Ireson et. al., 2002)

Although p.o, administered curcumin has poor bioavailability and only low or non-measurable blood levels were observed (Perkins, S. et al. *Cancer Epidemiol. Biomark. Prev.*, 2002, 11: 535-40), this route of administration inhibits chemically induced skin and liver carcinogenesis (Chiang, S. E. et al, *Carcinogenesis*, 2000, 21: 331-35). Oral administration of curcumin also inhibits the initiation of radiation-induced mammary and pituitary tumours (Inano, H. et al, *Carcinogenesis*, 2000, 21:1835-41). Similarly in a study to assess the curcumin levels in the colorectum, a daily dose of 3.6 g curcumin achieves pharmacologically effective levels in the colorectum with only negligible distribution of curcumin outside the gut, blood and liver tissues (Garcea, G. et al, *Cancer Epidemiol. Biomark Prev.*, 2005, 14:120-25).

The factors that limit the curcumin absorption are the rapid glucuronidation/sulfation of curcumin's phenolic hydroxyl group, the instability of curcumin in aqueous solution at pH 7 and above and hydrophobicity and insolubility in water at acidic pH, when delivered as a dry powder in existing supplements. Most curcumin is never absorbed and simply passes through the GI tract and is excreted (Anand et al, 2007, 4(6), 807).

The prior art in the field is pure curcuminoids which is readily conjugated in the intestine and liver to form curcumin glucuronides and curcumin sulfates or reduced to hexahydrocurcumin. High dosage like 3 to 4 g per Kg, fails to achieve detectable plasma levels in humans and itself explains limited success rate in translating the in vitro results to the clinic.

US Patent Application 1998/5744161 describes the administration of piperine along with curcumin enhances the bioavailability of curcumin. However the level of enhancement was only modest and no curcumin could be detected after 3 hours even when supplemented with piperine. This approach has its disadvantage as most glucuronidation takes place in the upper GI tract, where the pH is acidic and curcumin is not completely dissolved until pH 8.5 and higher. In addition, the formulation acts by inhibiting the glucuronidation, which may cause serious health risks, as glucuronidation is protective against many toxins and involved in the metabolism of commonly used drugs.

Another prior art is US Patent Application US20070148263 in which the invention relates to a formulation of curcuminoid with the essential oil of turmeric to enhance the bioavailability of curcumin and to augment the biological activity of curcumin. In this formulation, Ar-turmerone, the main constituent of the essential oil was reported to be responsible for the enhanced bioavailability of curcumin. The disadvantage of this invention is that this formulation also acts by inhibiting glucuronidation.

Yet another art WO 2007103435 involves the formulation comprising curcumin, an antioxidant, a water solubilising carrier, and optionally a glucoronidation inhibitor forming a curcuminoid-lipid micelle and finally provides as an emulsion or solid-lipid nanoparticles. The method claims to have 5-times bioavailability in animals upon 100 mg/kg level supplementation, as compared to normal curcumin. Though this method claim to have more than five times bioavailability upon 100 mg/kg level supplementation, as compared to normal curcumin, the final composition contain only 2 to 3% curcumin, which may require substantial amount of consumption, even to achieve 100 mg/kg level. Moreover, the clinical safety of nanoparticles for consumption has not been finalised so far.

Another art WO 2007101551 involve phospholipid complexes of curcumin for improved bioavailability. In a study conducted on rats, peak plasma levels and area under the plasma concentration time curve (AUC) values for parent curcumin after administration of curcumin complexed with phospholipids were only five-fold higher than the equivalent values seen after treatment.

Though a minimum concentration of 0.1 µM curcumin in plasma was established for the in vitro efficacy, the oral delivery of even 3.6 g to humans could detect only nanomolar in vivo levels, after an hour of consumption (Sharma et al., 2004). Marczylo et al (2007) have reported a plasma concentration of 6.5±4.5 nM after 30 min of oral administration at 340 mg/kg on rats. Many attempts based on adjuvant, liposomes, micelles, phospholipid complexes and nanoparticles have also been reported to circumvent the problems of poor bioavailability of curcuminoids (Anand et al., 2007).

SUMMARY OF THE PRESENT INVENTION

The present invention relates to a new fenugreek derived polysaccharide (composed of galactose and mannose units, referred to as galactomannans) containing fenugreek proteins. Fenugreek polysaccharide containing proteins was found to enhance the bioavailability of curcumin both in preclinical studies and in studies on human volunteers when formulated as amorphous microgranulate dispersions with proper molecular binding with curcuminoids. Fenugreek polysaccharide used in the present invention is non digestible, but swell extensively in the intestine and form a gel matrix in which curcumin is impregnated and leaches out very slowly. The advantage of the present formulation of micro granulate is that when consumed, it is very stable under physiological conditions and protect curcumin from easy access to enzymes responsible for its rapid degradation.

In a prior art, U.S. Pat. No. 6,063,402, describes the preparation of highly pure galactomannans from commercially available guar gum from guar seeds and its use as a pharmaceutical excipient; particularly for the tablets with increased hardness characteristics. The invention does not consider fenugreek derived galactomannans nor about its capacity as a controlled release matrix.

Another prior art in the field is US Patent Application 2008/0206340 which relates to a method for increasing the bioavailability of nutrients using Guar meal and Konjac meal containing galactomannan/glucomannan and for introducing the active substances, e.g. the human growth hormone HGH and others, into the human or animal metabolism. The patent is in broad terms. The patent does not mention about curcumin, its mode of incorporation or the kinetics of absorption/resorption into blood up on oral delivery. The invention does not claim the use of fenugreek matrix for the slow release of curcumin. Fenugreek derived galactomannan has not been mentioned anywhere, and no such studies have been published. Curcumin is a unique phytochemical (plant isolate) with regard to its very low absorption and fast degradation in blood, compared to the other nutrients and herbal isolates in general and stands apart from other herbal isolates and nutrients. The invention neither mentions about the increment in bioavailability one can expect from the formulation, nor does it specify about curcumin or about its enhancement in efficacy due to enhancement of bioavailability. Mannans to galactose ratio, molecular weight and the mode and place of linkages of galactose moieties to the mannan backbone are usually different in galactomanns derived from various legumes and hence there is difference in physical properties, which has a material effect on the invention. Fenugreek galactomannan has the maximum amount of galactose, the ratio being 1:1. Thus, galactose and mannose residues in fenugreek galactomannans are uniformly linked to provide maximum hydration and solubility which in turn helps to minimise chain entanglement. Curcumin molecules can thus uniformly interact with galactomannan chains, rather than the near entrapment of the molecules within the galactomannan agglomerates as detailed in US Patent 2008/0206340. The molecular binding, nature of entrapment, surface topography, and stability of granulates under physiological conditions were characterised by DSC, PXRD and SEM analysis.

The advantage of this invention over the prior art is that the present invention provides curcumin impregnated amorphous micro encapsulates in which hydrophobic curcuminoids are uniformly entrapped and bonded with the soluble fibre galactomannans containing proteins to produce more water soluble, compatible and stable forms. The advantage of the present invention over the prior art is that it is a formulation of curcumin and fenugreek which helps to overcome the major limitations of curcumin, viz. the poor bioavailability upon oral delivery; the absorption of curcumin in blood takes place to a physiologically relevant level for considerable duration for delivering its health benefits. Both are non toxic and both have got independent health benefits.

An advantage of the present invention over the prior arts as shown from an animal study was that, curcumin from the present invention absorbs almost 20 times more than normal 95% pure unformulated curcumin, on an average when the area under curve calculations for plasma curcumin concentration verses time plot was considered. Moreover, $T_{max}$, (time taken to reach maximum concentration in plasma) for the new formulation was 5 hour as compared to unformulated curcumin $T_{max}$ of 3 hour. Further more, curcumin is present in the blood plasma even after 24 hour, ($C^{24}_{max}$) in an average of 0.21 ug/g level when the new formulation is consumed, in comparison with 0.008 ug/g for unformulated curcumin.

In a pilot study conducted on human volunteers, curcumin absorption to the blood from the present invention was almost 15.8 times greater than from the unformulated curcumin of 95% purity. Maximum absorption of curcuminoids in the plasma was observed within 60 min as compared to normal curcumin which was around 30 min. Furthermore, presence of curcumin at 0.48 ug/g level was observed in the plasma even after 24 hour consumption of the present invention product. It was only 0.004 uM or even less with 1 g of normal unformulated curcumin consumption.

Another advantage of the present formulation is to provide amorphous curcumin by ultrasound mediated gel-phase microencapsulation in fenugreek soluble fiber matrix.

Another advantage of the present invention is that it increases the solubility of curcuminoids as it can form a viscous solution in water in which curcumin can be uniformly suspended in a colloidal form.

Another advantage of the present formulation is the use of galactomannans of optimum hydrophobic-hydrophilic balance as evident from its water and oil binding capacity to encapsulate colloidal form of curcumin produced by sonication, homogenisation and the like to provide gastrointestinal fluid compatible formulated curcumin.

Another advantage of the present formulation is the use of galactomannan fibers to protect from degrading enzymes in upper gastrointestinal tract and to extensively swell in gastrointestinal fluid to slowly release the bound curcumin.

Yet another advantage of the present invention is that it can also work as a supplement of healthy soluble dietary fiber, which is playing a vital role as a prebiotic fiber.

Yet another advantage of the present invention is to provide as nontoxic formulation of curcumin, employing food grade phytochemicals derived from GRAS (Generally regarded as safe) plants as evident from the toxicity studies in rats, which is capable of enhancing the effective absorption of curcumin into blood upon oral administration.

Yet another advantage is its directly compressible nonhygroscopic powder form for easy handling and formulation in tablet and capsule forms.

The present invention seeks to overcome these limitations in the background of the invention.

Object of the Invention

An object of this invention is to derive full benefits from the administration of curcumin in human subjects.

Another object of this invention is to propose a new formulation which enhances the bioavailability of curcumin.

Another object is to provide an enhanced bioavailable formulation of curcuminoids using only food grade, inexpensive and easily obtainable materials by preventing the rapid enzymatic degradation in vivo and the increasing solubility and compatibility of curcuminoids in gastrointestinal conditions.

Still another object of the invention is to propose a new formulation which will not retard glucuronidation but at the same time enhances bioavailability of curcumin.

A further object of this invention is to propose a new formulation which enhances the concentration of curcumin in the blood for longer duration.

Further objects and advantages of this invention will be more apparent from the ensuing description.

The present invention relates to the enhanced bioavailability of a judiciously executed formulation of curcumin using a non-digestible, but fermentable soluble dietary fiber galactomannans containing protein isolated from the common curry spice, fenugreek. Oral administration of curcumin-impregnated soluble fiber, dispersions enhanced the bioavailability 20 times at 250 mg/kg dosage in animals and human hepatic bioavailability improved 12.9 times at a dose of 250 mg (equivalent to 100 mg curcumin) and 15.8 times at 1500 mg (equivalent to 600 mg curcumin) as compared to unformulated curcumin dosage of 1000 mg when the area under plasma curcumin concentration-time curve was considered. Curcumin-impregnated soluble fiber microgranulates showed amorphous character and better hydrophobic-hydrophilic balance for swelling and slow release of stable colloidal curcumin for improved absorption. Ultrasound was found to be a novel tool for the particle size reduction and homogeneous distribution of colloidal curcumin in the fiber solution.

DETAILED DESCRIPTION OF THE INVENTION

According to this invention there is a novel fenugreek derived polysaccharide dietary fiber containing fenugreek proteins which enhances the bioavailability of curcumin when formulated in amorphous microencapsulates of proper molecular binding with each other, following oral administration and which differ significantly in its properties with regard to efficacy.

The present invention relates to a formulation containing curcuminoids exhibiting enhanced in vivo bioavailability and resultant improved efficacy, said formulation comprising curcuminoids and a gel forming, non digestive soluble dietary polysaccharide fiber galactomannan and proteins derived from fenugreek [*Trigonella Foenum graecum*]. Further curcuminoids are impregnated in said fiber matrix. Inventors have found that the formulation comprising curcuminoids and a gel forming, non digestive polysaccharide fiber galactomannan containing protein is synergistic in nature as it increases the bio availability of curcuminoids in vivo for substantially long period.

The present invention also relates to a process for producing a formulation containing curcuminoids exhibiting enhanced in vivo bioavailability and resultant improved efficacy comprising a gel forming, non-digestive, but fermentable soluble dietary polysaccharide fiber galactomannans and proteins derived from fenugreek (*Trigonella Foenum graecum*) by suitably grinding or mixing the water dispersed colloidal curcuminoids aqueous fenugreek fiber dispersions under ultrasound mediated mixing (sonication), homogenisation and the like, to produce curcuminoid encapsulated fiber dispersions. Further sonication or homogenisation is carried out at 50° C. to form a uniform viscous solution of curcuminoids dispersed in said fiber gel phase.

The present invention also provides a process for the preparation of colloidal curcumin encapsulated fiber dispersions as amorphous and water miscible microgranulates of uniform size and density by drying the above aqueous dispersions under vacuum and below 80° C. employing techniques such as rotory drying followed by granulation or spray drying.

Dried rhizomes of turmeric were powdered and extracted with a mixture of hexane and acetone and solvent was evaporated to get a pasty mass called turmeric oleoresin. Other solvents like ethylalcohol, ethyl acetate, ethylene chloride or their mixtures thereof can also be used for the extraction. The oleoresin was then dissolved in varying compositions of ethanol, isopropanol or mixtures thereof to crystallize curcuminoids with 85 to 95% purity, and was filtered and dried under vacuum at 70° C. It was pulverized to get curcumin powder of 85-95% purity with an average particle size of 150-250 microns. Purity was determined by the method of JECFA 2003 method (Joint Expert Committee on Food Additives), by measuring the absorbance at 420 nm in acetone.

Soluble fiber galactomannans was isolated from fenugreek seeds. Briefly, matured fenugreek seeds were flaked and successively extracted with ethanol to produce debittered and deodourised fenugreek seeds by removing the phytochemicals such as alkaloids, saponins, flavanoids etc. It was then dried to remove the solvent and subject to differential grinding and sieving to separate the endosperm of fenugreek seeds containing the galactomannan fiber and proteins from the seed coat. White endosperm powder thus obtained is dissolved in excess of water and the galactomannan fraction was precipitated along with proteins by the addition of calculated quantity of ethanol. The precipitate was filtered and the process of dissolution in water and re-precipitation with ethanol was repeated, if required, to get minimum 80% soluble fiber content upon enzymatic-gravimetric analysis (AOAC 2000 ed., Enzymatic Gravimetric analysis of dietary fiber, Method No. 985.29) and minimum 5% protein content as determined by Kejndhal method. It was ground to 125 microns and dissolved in 10 times excess of water (w/v), with the aid of sonication or homogenization, to a uniform viscous solution.

Various percentage formulated curcumin were then prepared by ultrasound mediated gel-phase dispersion of curcuminoids in fiber matrix. Briefly, curcumin powder required to form minimum 25% weight percentage and maximum 60% weight percentage was suspended in 5 to 10 times excess of water containing 1% weight of hydroxypropylmethyl cellulose or carboxymethyl cellulose solution and 10% (w/v) glycerine, with the aid of sonication at below 70° C. Solution can also be subjected to high pressure homogenization at a pressure above 400 psi to produce uniform colloidal curcumin dispersion in water. Curcumin solution was then slowly mixed with the fiber solution. Care was taken to keep the temperature below 50° C. during ultrasound-mediated mixing. Cloudy yellow aqueous solution thus obtained was dried under vacuum at 60-70° C. and the resulting yellow flakes were milled and sifted to produce uniform microgranulates of 150±20 μm in size. The procedure was repeated to produce formulated curcumin containing various percentages of curcumin, ca. 20, 40, and 60 (w/w).

The present invention also relates to a process for extracting non-digestible soluble dietary polysaccharide fiber galactomannans containing a suitable concentration of fenugreek proteins from fenugreek seeds [*Trigonella Foenum graecum*] comprising the steps of, wet differential grinding of water soaked fenugreek seeds followed by sieving to separate the fiber and protein rich endosperms followed by alcoholic extraction for effective debittering, deodourising to produce fenugreek galactomannans containing proteins. Dissolution of fiber followed by alcoholic precipitation is carried out, if required, to produce purified polysaccharide galactomannnas fiber with a protein content of 5-15% (w/w).

The present invention is illustrated by the working examples given below. It is to be understood that the specific examples being given here are by way of illustration and are not intended to be taken restrictively to imply any limitation on the scope of the present invention.

EXAMPLES

Example 1

5 Kg of dried turmeric rhizomes were flaked in a mechanical flakier and extracted with 20 liter acetone-hexane mixture, (80/20 v/v) in a stainless steel vessel for 4 to 12 hours. The extraction was repeated 4 times under similar conditions and the filtrate was evaporated to dryness using a rotary evaporator at 50° C. Crude pasty mass thus obtained (1000 g) was found to contain 32.4% curcuminoids by JECFA method employing UV/Vis spectrometric estimation of absorbance at 420 nm in acetone. The crude mass was then mixed with 0.5% w/v of isopropyl alcohol and kept for 3 days at room temperature. Crystallized curcuminoids are then separated by centrifugation, washed with isopropyl alcohol and dried to get 208 g of 92% pure curcuminoids. The same extraction and crystallization were repeated in ethyl alcohol to get 186 g of 91.2% curcuminoids. Above crystallization were further repeated to get more than 95% pure curcuminoids.

2 Kg of fenugreek seeds were swelled in water and subjected to wet grinding and sieving to separate the endosperm from the outer shell. Endosperm was further extracted with ethanol to remove the characteristic smell and bitter taste of fenugreek and then dried. The isolated fiber was then dissolved in 10 times excess of water and precipitated with ethyl alcohol. The precipitate was filtered, dried under vacuum, uniformly powdered. Yield: 354 g (17.7%), 87% fiber content upon enzymatic-gravimetric analysis and 11.4% protein content upon Kjendhal's method.

Curcumin impregnated soluble fiber microencapsulates were prepared by ultrasound mediated gel-phase microencapsulation of curcuminoids in fiber matrix. 400 g of curcumin with minimum 91% purity was suspended in 4000 ml water containing 40 g of hydroxypropylmethyl cellulose and 400 g of glycerine with sonication using 1000 W ultrasound generator for 1 hour at intervals of 10 minutes keeping the temperature below 70° C. 600 gm of soluble fiber with 90% galactomann content and 12% protein content was then mixed with 3000 ml of water with the aid of sonication for 1 hour at interval of 10 minutes to form free flowing uniform gel phase. The above curcumin solution was then mixed to the fiber in small portions of 50 ml with constant sonication keeping the temperature below 50° C. The cloudy yellow viscous water solution thus obtained was dried under vacuum and the dried flakes thus obtained were passed through an oscillating granulator and sifter to produce the uniform granulates of 150±20 µm. The solution can alternatively spray dried to produce water compatible microencapsulates of curcumin. The enhanced efficacy of novel formulation of curcumin, was further investigated in animals and humans.

Example-2

Figure 1:
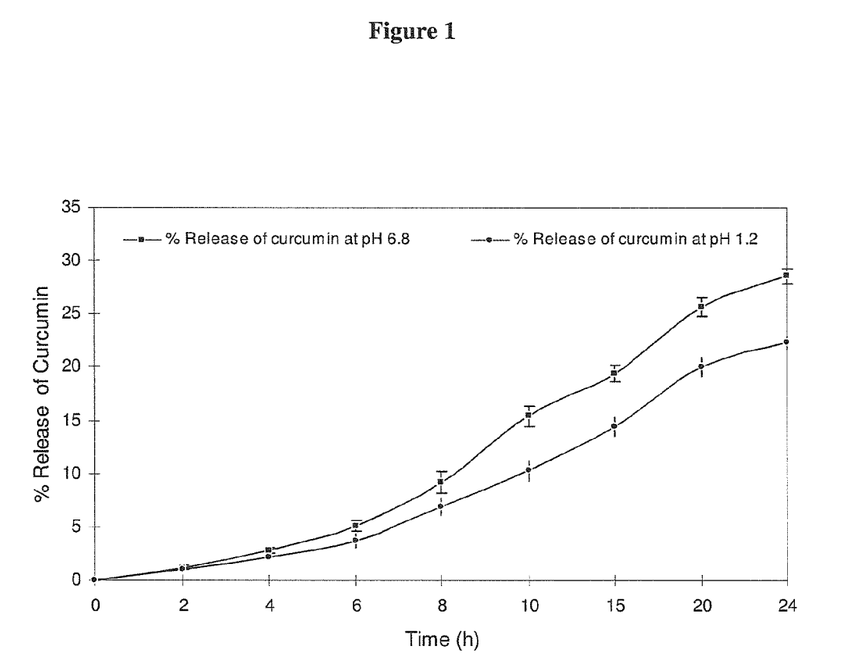
FIG. 1 In vitro release of curcumin from curcumin-impregnated soluble fiber microgranulate containing 60% (w/w) fiber at pH 1.2 and 6.8, at 37° C. Each data point is an average of 3 measurements (n=3) performed under identical conditions.

The in vitro release profile of the loaded curcumin from the new formulation at pH 6.8 and pH 1.2 (to simulate stomach and colonic conditions) is illustrated in FIG. 1. 50 mg of formulated curcumin was dispersed in 10 ml phosphate buffer at pH 6.8 and 0.1M HCl at pH 1.2 for 24 hours and was kept in a sealed thermostated water bath set at 37±0.5° C. under constant shaking. 500 micro liter (µl) of solution was carefully withdrawn from the mixture without contamination of the curcumin particles and made up to 50 mL with acetone and the absorbance was measured at 420 nm using UV/VIS spectrophotometer. The concentration of the released curcumin was then calculated using a standard curve of curcumin in acetone. From the calibration curve plotted for absorbance verses concentration, the release kinetics of entrapped curcumin with time was estimated. Studies were performed in triplicate and mean cumulative percentage of released curcumin was calculated and plotted against time.

Cumulative percent of release of curcumin from unformulated curcumin powder was only 0.08% (pH 6.8) and 0.06% (pH 1.2) after 24 hour, due to insolubility of curcumin in water. The release testing of curcumin from formulated curcumin containing 60% (w/w) fiber, showed percent release of only 5.1±1.2 at pH 6.8 and 3.7±0.9 at pH 1.2 in the initial 5 hour; indicating an increased solubility and water compatibility of curcumin when impregnated and uniformly dispersed in fiber matrix, as compared to unformulated curcumin. On continuation of the release study, curcumin release was prolonged and found to increase with time in a steady and sustained manner, such that 28.6±1.8% was observed at pH 6.8 and 22.3±2.1% at pH 1.2 (FIG. 1). Thus the release of curcumin from formulated curcumin was very little during the initial hours with a lag time of more than 5 hours and the total release was less than 30% even after 24 h. This could be attributed to the very slow initial swelling of polysaccharide chains in water and its further dissolution to allow the leaching of entrapped curcumin into the solution in the dissolution flask. Delayed lag time has shown to provide protection to drug in the gastrointestinal tract, as already proved in high viscosity hydroxypropylmethyl cellulose coated systems with slow drug release colonic delivery (Patel et al., 2009). Normal curcumin, on the other hand is completely insoluble with macroparticles floating on the surface and showing around 0.4% curcumin dissolved after 24 hours. Increase in dissolution rate of formulated curcumin can be attributed to change in the high energy amorphous state during the formation of dispersion and the increased viscosity of the binary system decreases the diffusion of drug molecules necessary to form crystal lattice.

Example-3

The enhanced efficacy of the invention was tested in animal studies and in human volunteers. Formulated curcumin containing 40% curcumin microencapsulates were selected for animal studies. Male Wistar albino rats 200-250 g body weight, were fasted overnight and received either normal curcumin or formulated curcumin dissolved or suspended in a suitable aqueous solution containing 0.1% carboxymethylcellulose, at 250 mg/Kg body weight by oral gavage. At 30 minute post dose, animals were exsanguinated and blood was collected after each time point, ca. 0, 0.5, 1, 3, 5, 10 and 24 hours respectively into heparinized tubes and centrifuged at 6000×g for 15 minutes. Plasma was decanted and stored at −80° C. until analysis. Plasma samples at various time points up to 24 hour post administration were subjected to Concentration of curcumin in plasma at each time point was calculated as an average of sixteen HPLC measurements using methanol mobile phase which eluted total curcumin (free curcuminoids plus its metabolites) as a single peak at retention time 2.9 min (US 2007/0148263). Briefly, 1 mL of plasma was extracted with 3×10 mL of ethyl acetate and is dried over anhydrous sodium sulphate and evaporated to dryness. The residue was then made up to 10 mL with methanol and 20 µL was injected to Shimadzu model LC-20 AT HPLC fitted with a PDA detector model M20A using a reverse phase C18 column (Phenomenex 250×4.6 mm, 5µ) and methanol mobile phase monitored at 420 nm.

Figure 2:
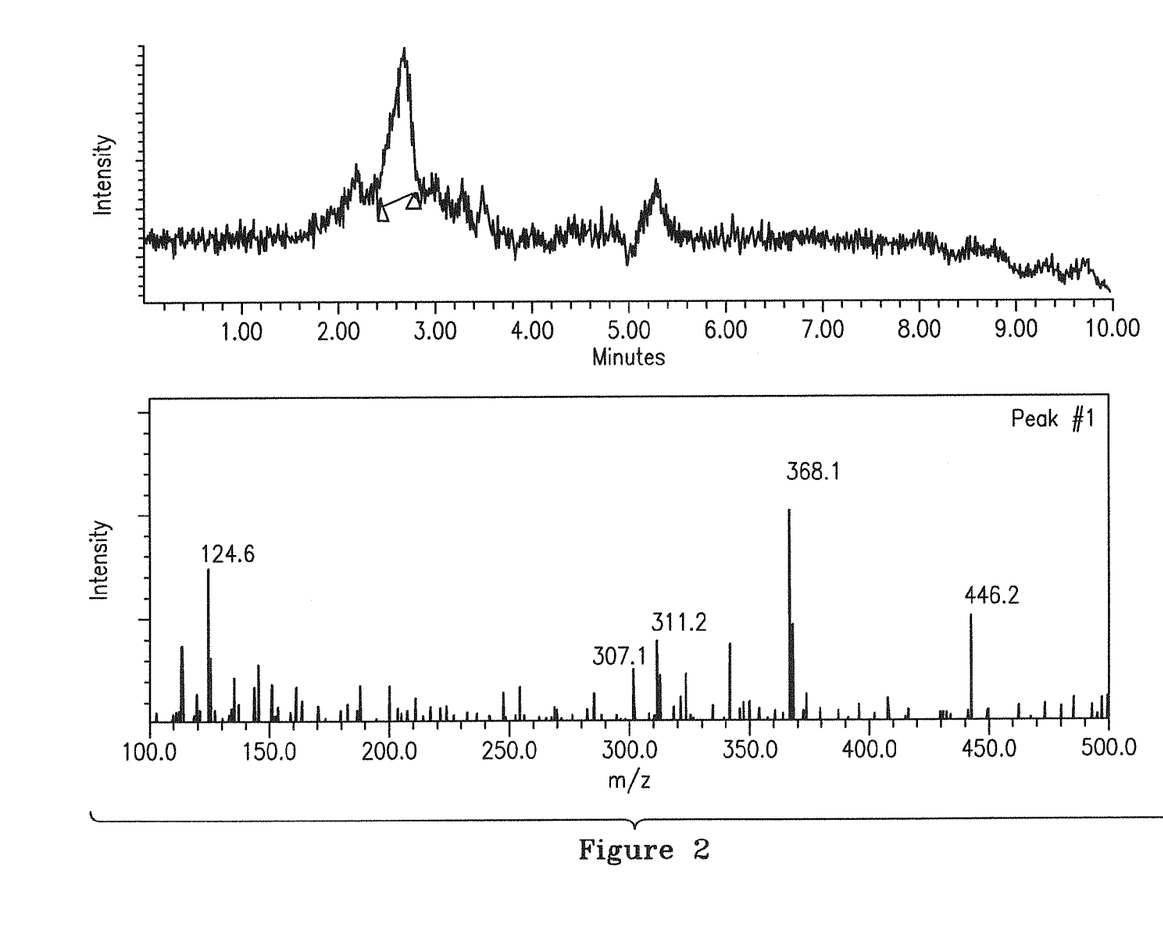
FIG. 2 shows the authenticity of curcumin appeared in plasma HPLC analysis as confirmed by LC/MS.
Figure 3:
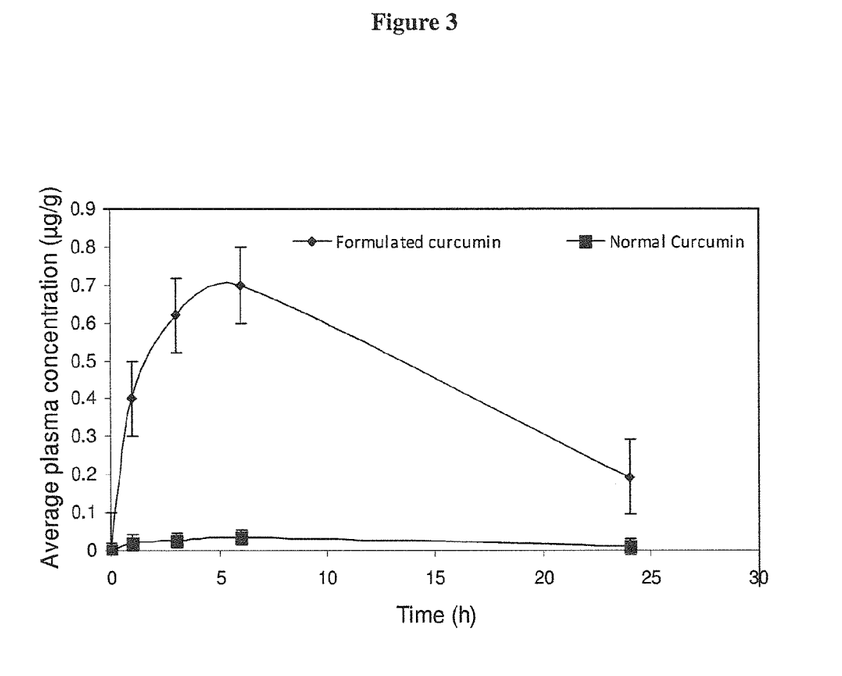
FIG. 3 Average concentration of curcumin observed in rat plasma after oral administration of curcumin-impregnated soluble fiber microgranulate containing 60% (w/w) fiber and unformulated curcumin at 250 mg/kg dosage. The data is expressed as the mean±SD from n=16 rats used as two groups of eight animals each. *p<0.05 and **p<0.01, (250 mg/kg formulated curcumin vs 250 mg/kg unformulated curcumin). Concentration was determined by HPLC/PDA detection.

Measurement of curcumin content in plasma was validated by spiking a standard curcumin (CAS Registry No. 458-37-7) in animal blood and plasma at 1.0 µg/mL. Curcuminoid retention time was confirmed by repeated 10 analyses at 50 mg level on same column under identical conditions. Efficiency of extraction from blood and plasma was also confirmed by spiking 1 mg/mL standard curcumin. Range and linearity were determined for curcumin extracted from blood and plasma as mentioned above and the recovery of curcuminoids were calculated to be 89 and 91% respectively. Plasma samples at various time points up to 24 hour post administration were subjected to HPLC-PDA analysis, after confirming the detected peak identity using an electrospray ionization mass spectrometer in negative ionization mode, which could detect molecular masses corresponding to protonated curcumin at 368 (FIG. 2). Analysis was performed by incorporating a Waters Alliance LC fitted with Waters 3100 ESI mass detector.

Example 4

The enhancement of bioavailability was also tested on human volunteers of age group between 25 to 50, who were healthy and not involved in any medication or health supplementation. The volunteers were not allowed to take turmeric-containing food for two days prior to the test.

8 volunteers were given 250 mg (250 mg×1) and 1500 mg (250 mg×6) of formulated curcumin. 6 mL blood of each volunteer was withdrawn at 0, 0.5, 1, 3, 5, 8 and 24 hours respectively and plasma samples were deep-frozen at −80° C. till analysis. 1 mL of the plasma was then analysed for curcumin content by HPLC as was done for animal studies. After one week of formulated curcumin feeding, the volunteers were also given 1000 mg (500 mg×2) of normal curcumin and protocol was repeated exactly the same for collection and analysis of blood samples at various time intervals. Curcumin content found in the whole blood and plasma of 8 volunteers upon oral administration of 1000 mg of normal curcumin of formulated curcumin was shown in FIG. 4.

Figure 4:
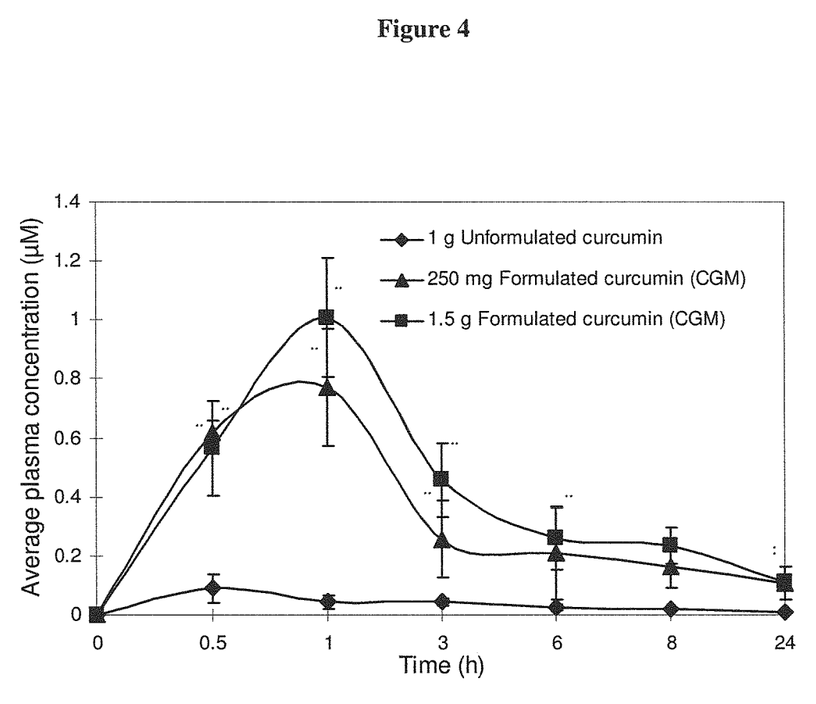
FIG. 4 Average concentration of curcumin observed in human plasma after oral administration of curcumin-impregnated soluble fiber microgranulate containing 60% (w/w) fiber at doses of 250 mg and 1500 mg. Unformulated curcumin was administered at 1000 mg dose. The data is expressed as the mean±SD (n=8); *p<0.05 and **p<0.01, (250 mg and 1500 mg formulated curcumin vs 1000 mg unformulated curcumin) Concentration was determined by HPLC/PDA detection.
Figure 5:
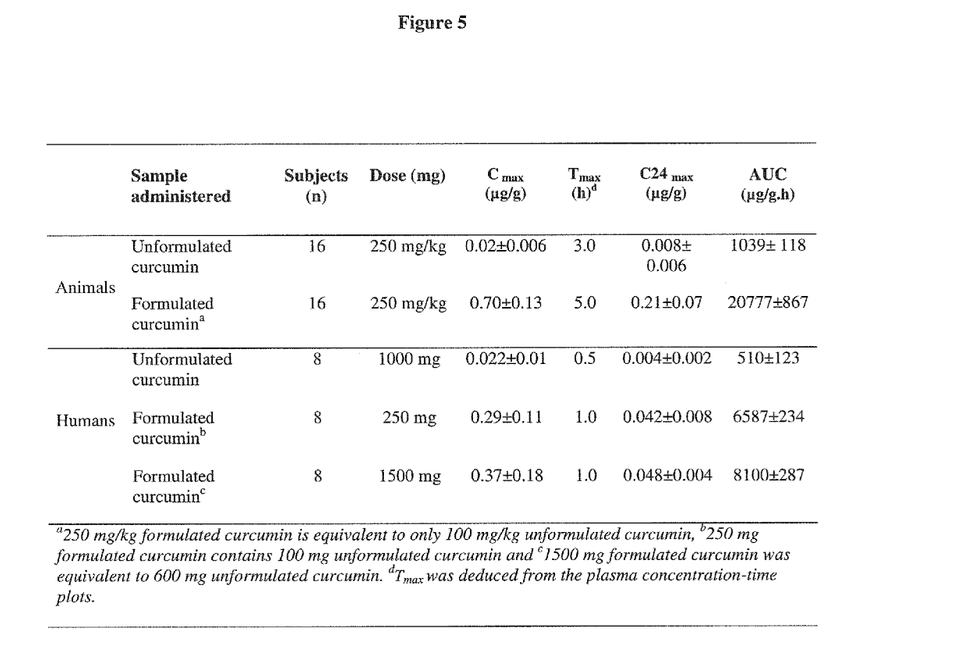
FIG. 5 shows the Table of pharmacokinetic parameters of formulated curcumin at various dosages (animals and humans).

A considerable enhancement, almost 12.9 times as evident from the area under curve calculations, on an average, was observed after consumption of 250 mg of formulated curcumin (FIG. 4). When the same was repeated with 1500 mg of formulated curcumin to get an effective concentration of 600 mg curcumin, the increase in blood and plasma curcumin concentration was observed to be 15.8 times as compared to 1 g of normal curcumin (FIG. 4). The maximum concentration of curcumin was attained in plasma within 1 hour ($T_{max}$). Thus on a comparison of pharmacokinetic parameters like maximum curcumin concentration in plasma ($C_{max}$), the time taken to reach the maximum concentration ($T_{max}$) and concentration of curcumin in blood after 24 h ($C^{24}_{max}$), as shown in FIG. 5, it can be seen that curcuminoids in the new formulation stays in the intestine for long time and releases slowly to effect a continued absorption into blood stream to produce 15.8 times more curcuminoids in blood as compared to unformulated curcumin.

Curcumin impregnated galactomannan microgranulates were found to offer the efficacy by improving the hydrophobic-hydrophilic balance to increase the solubility, compatibility and stability under gastrointestinal conditions whereby providing a slow and controlled release of impregnated curcumin into the blood stream upon extensive swelling in the gastrointestinal tract. Soluble dietary fiber is an extensive gel forming nondigestible hydrocolloid which undergoes fermentation in the colon by the action of β-mannanase and may provide protection to curcumin from the degrading enzymes of the upper gastrointestinal tract.

Ultrasound mediated gel-phase dispersion was employed to produce highly amorphous curcumin-impregnated soluble fiber microgranulates, with enhanced aqueous solubility, stability, compatibility and slow release kinetics under physiological pH. Techniques like high pressure homogenization may also be employed for the uniform suspension and impregnation of curcuminoids in fiber matrix. The presence of HPLC detectable curcuminoids in the plasma after even 24 hours indicates its stability and slow release mechanism in vivo thus enhancing efficacy and differing significantly in its properties with regard to efficacy.

Example 5

Standard curcumin (CAS Registry No. 458-37-7) was purchased from Sigma-Aldrich, Bangalore, India. All solvents and reagents for analysis were of HPLC grade and that for extraction were of analytical grade from Merck, Mumbai, India. MilliQ Plus (Millipore) purified water was employed for all experiments. Sonication was performed using 1000 W ultrasound generator fitted with a sonotrode (Hieilscher, Germany). UV/VIS analysis was performed on Varian-Cary 5000 UV-VIS-NIR spectrophotometer (Varian Inc, Chennai, India). Thermogram was recorded using Q10 DSC, differential scanning calorimeter (DSC Metier Toledo 822e), Mettler-Toledo India Pvt Ltd, Mumbai, India. Samples (3-5 mg) were sealed in the aluminum crimp pan, and heated at a rate of 10° C./min from 30 to 300° C. under a nitrogen atmosphere. Powder X-ray diffraction studies (PXRD) were performed on a Bruker D8 Advance instrument: target Cu, λ-1.54 A°, filter-Ni, voltage 40 kV, time constant 5 min/s; scanning rate 1°/min (Bruker AXS GmbH, Karlsruhe, Germany). Scanning electron microscopic analysis was done on SEM Jeol 6390 LA equipment (JEOL Ltd, Tokyo, Japan). HPLC analyses were carried out on a Shimadzu LC 20 AT system, with M20A Photo diode array (PDA) detector ((Shimadzu Analytical Pvt ltd, Mumbai, India), fitted with a reverse phase C18 Phenomenex column (250×4.6 mm, 5μ) using methanol as the mobile phase. LC/MS was performed on Waters HPLC (Alliance system, with MassLynx software) fitted with 3100 ESI mass detector (Waters Ltd, Bangalore, India).

Figure 6:
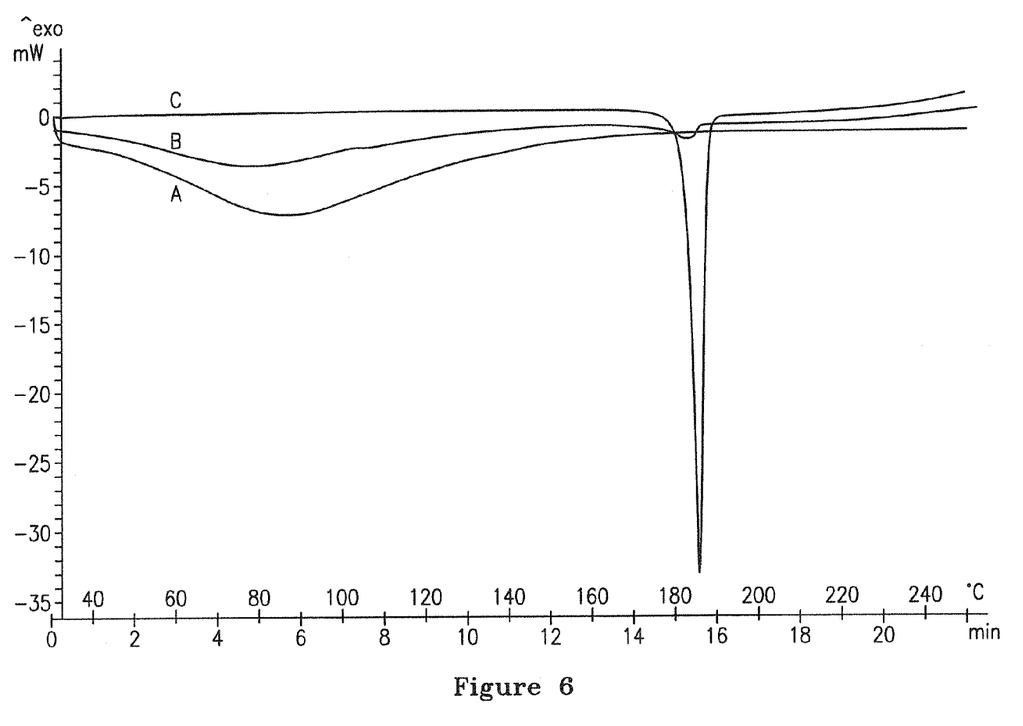
FIG. 6 Differential Scanning calorimetry (DSC) thermograms of (A) soluble fiber from fenugreek (B) curcumin-impregnated soluble fiber microgranulate containing 60% (w/w) fiber, (C) curcumin.

Stability, crystallinity and curcumin-fiber interactions were assessed by differential scanning calorimeter (DSC), Powder X-ray diffraction (PXRD), investigations of unformulated curcumin, fenugreek-derived soluble fiber, formulated curcumin with 20, 40 and 60% (w/w) fiber and the corresponding physical mixtures. Physical mixtures were prepared by mixing appropriate percentage of curcumin and fiber powder in water without sonication and drying under vacuum at 60° C. DSC studies showed a sharp endotherm at 186° C. for pure curcumin due to its melting, whereas the soluble fiber exhibited no peaks. Neither the nature nor the position of endotherm showed a change when formulated as physical mixture, though a decrease in intensity proportional to the percentage composition was observed (data not shown). All samples except pure curcumin, showed an endothermic shift around 95° C. due to the residual moisture content in the fiber matrix. In the case of formulated curcumin, the endothermic peak broadened, reduced intensity and was shifted to lower temperature with increase in fiber content. The change was very evident at 60% (w/w) fiber containing formulated curcumin, where the endotherm appeared at 174° C., indicating its predominantly amorphous nature (FIG. 6).

Figure 7:
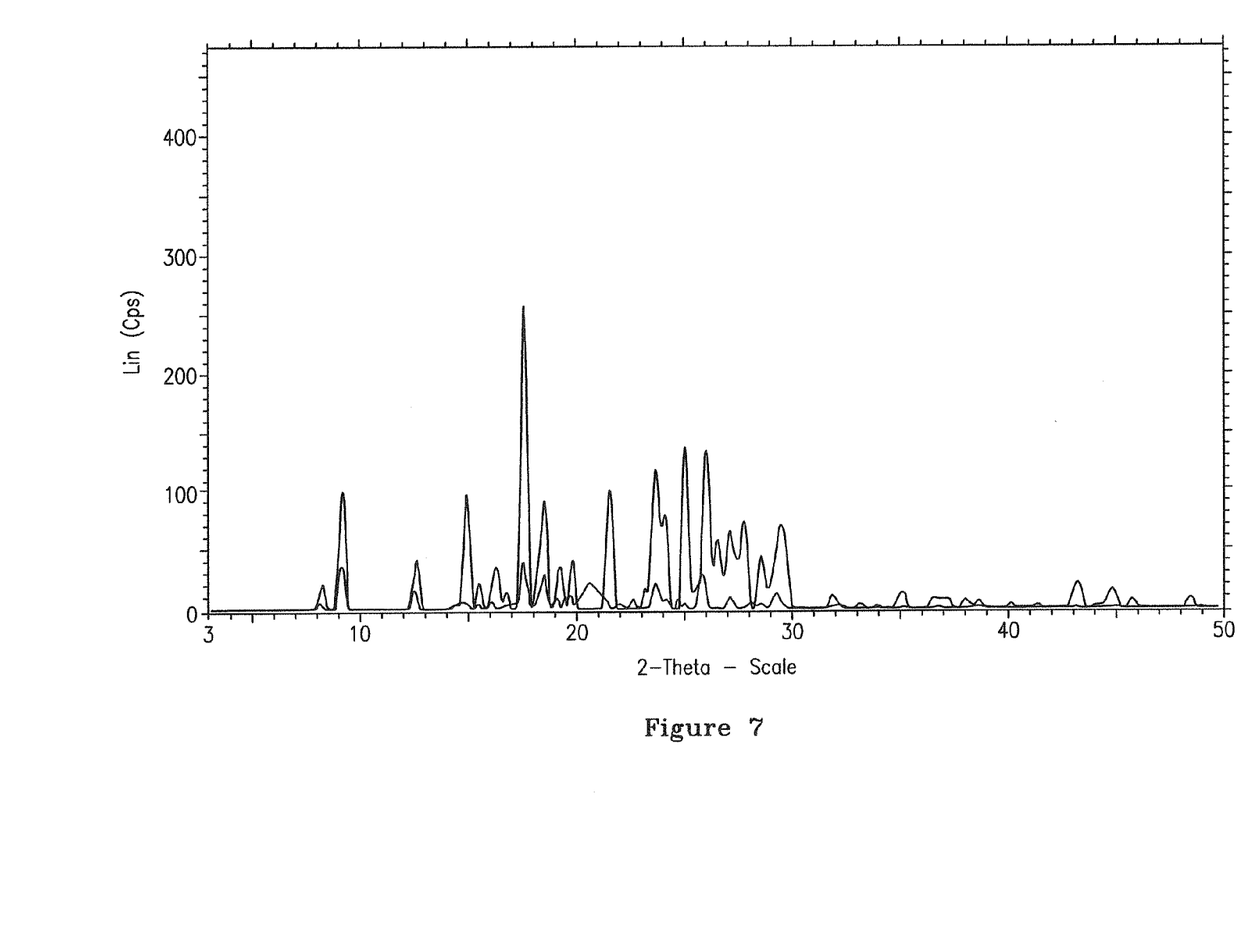
FIG. 7 Powder X-ray diffraction (PXRD) spectra of soluble fiber from fenugreek (dark) curcumin (grey—sharp peaks) and curcumin-impregnated soluble fiber microgranulate containing 60% (w/w) fiber (dark—broad peaks).
Figure 8:
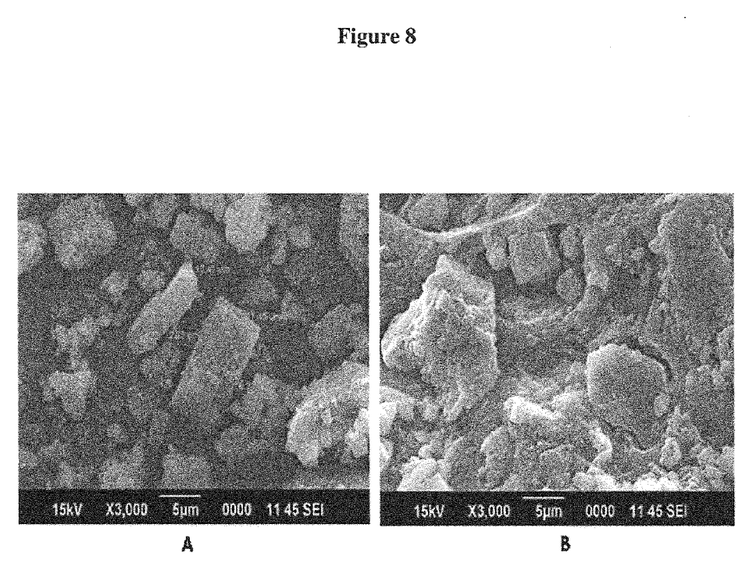
FIG. 8 Scanning Electron Micrograph (SEM) of (A) curcumin (B) curcumin-impregnated soluble fiber microgranulate containing 60% (w/w) fiber.

PXRD studies of curcumin showed sharp and intense peaks between 7 and 27° 2θ, whereas the soluble fiber gave typical amorphous pattern with just a broad less intense hill at 21° 2θ scattered angle. The physical mixtures showed characteristic pattern of curcumin, though with an elevated baseline and less intensity. In the case of formulated curcumin, a decrease in number and intensity of the peaks with a general broadening was observed with increase in percentage of fiber. In the case of 60% (w/w) fiber containing formulated curcumin, characteristic sharp peaks of curcumin observed at 15.1, 17.0, 19.3, 20.2, 21.5, 25.7 &26.6° 2θ were disappeared and the peaks at 9.3, 12.5, 17.4, 18.5 and 23.4° 2θ scattered angles becomes broad and less intense (FIG. 7). Thus it is clear that a considerable reduction in crystallinity of curcumin was occurred in fiber matrix confirming the encapsulation effect and more amorphous nature of curcumin-impregnated soluble fiber microgranulates. This was further evident from SEM photographs. Curcumin showed various shapes with well defined edges whereas the microgranulates prepared with 60% (w/w) fiber formed smooth, continues, highly porous surface in which amorphous curcumin was uniformly imbibed and dispersed in continues fiber matrix (FIG. 8).

It is to be noted that the invention is explained above with the help of an exemplary embodiment which is presented for the purpose of illustration and description in order to explain the various principles of the invention and their practical application. This is not intended to exhaust or limit the invention to a precise form that is disclosed and obviously many modifications and variations are possible in the light of the above teachings.

We claim:

1. A stable formulation comprising curcuminoids impregnated in non-digestive and soluble dietary polysaccharide fiber galactomannan matrix containing fiber content of 80-95% (w/w) and protein content of 5-15% (w/w) derived from fenugreek [*Trigonella Foenum graecum*] resulting into uniform curcumagalactomannoside particles wherein said formulation exhibits an enhanced in vivo bioavailability of at least 15 times more than curcumin alone.

2. The formulation of claim 1, wherein said curcumagalactomannoside particles are amorphous in nature.

3. The formulation of claim 1, wherein curcuminoids are derived from less than 60 weight percentage of dry curcumin powder suspended in excess water containing with or without hydrocolloids under ultrasound mediated ultrasonication, homogenisation or cryogenic grinding.

4. The formulation of claim 3, wherein curcuminoids are derived preferably from 20-60 weight percentage of dry curcumin powder.

5. The formulation of claim 1 wherein said polysaccharide fiber galactomannan matrix is obtained by subjecting water soaked and ground fenugreek seeds to alcoholic extraction to remove unwanted flavour and taste, discarding the alcoholic extract and subjecting said treated fenugreek seed mass to water extraction followed by addition of 2 to 5 times alcohol (v/v) to said aqueous extract to precipitate fiber and proteins, said precipitation process being repeated to produce substantially pure fiber and proteins, said fiber optionally being converted into free flowing gelly by employing ultrasonication.

6. A process for producing a stable formulation as claimed in claim 1, said process comprising the step of grinding a non-digestive soluble dietary polysaccharide fiber galactomannans and proteins derived from fenugreek (*Trigonella Foenum graecum*) in water under ultrasonication, 20 to 60% w/w of curcuminoids in said fiber resulting in uniform amorphous water soluble curcumagalactomannoside particles.

7. The process of claim 6, wherein the step of ultrasonication is carried out at 50° C. for different time intervals as pulses of duration from 1 to 3 minutes to form a uniform viscous solution of curcuminoids dispersed in said fiber gel.

8. The process of claim 7, wherein further comprising the step of evaporating the curcuminoids solution obtained after ultrasonication with said fiber under vacuum at 60-80° C. and granulated.

9. The formulation of claim 1, wherein the curcumagalactomannoside particles are of about 150±20 micrometers in size.

10. The formulation of claim 1, formulated for absorption in the intestine.

11. The formulation of claim 1, wherein the formulation provides stable curcuminoids at a temperature range of 90 to 120° C. and at a pH in the range of 2 to 7.5 in an aqueous solution.

12. The formulation of claim 1, wherein said formulation is a food grade formulation.

\* \* \* \* \*